United States Patent [19]

Ryan

[11] Patent Number: 5,344,407
[45] Date of Patent: Sep. 6, 1994

[54] SAFETY HOLDER FOR PRE-FILLED DISPOSABLE SYRINGE CARTRIDGE

[76] Inventor: Dana W. Ryan, 11520 SW. 22nd Ct., Davie, Fla. 33325

[21] Appl. No.: 57,536

[22] Filed: May 4, 1993

[51] Int. Cl.⁵ .............................................. A61M 5/32
[52] U.S. Cl. ................................... 604/192; 604/110; 604/263
[58] Field of Search ............... 604/192, 195, 263, 110, 604/187, 199, 197, 194, 196, 198, 231–232, 221–222, 218, 220, 242, 243; 128/766, 770, 919

[56] References Cited

U.S. PATENT DOCUMENTS

| | | |
|---|---|---|
| 2,740,404 | 2/1955 | Kohl . |
| 3,356,089 | 12/1967 | Francis . |
| 3,469,581 | 9/1969 | Burke . |
| 3,487,834 | 1/1970 | Smith, Jr. et al. . |
| 3,930,499 | 1/1976 | Rimbaud . |
| 4,140,127 | 2/1979 | Cianci et al. . |
| 4,168,699 | 9/1979 | Hauser . |
| 4,186,745 | 2/1980 | Lewis et al. . |
| 4,356,822 | 11/1982 | Winstead-Hall . |
| 4,383,530 | 5/1983 | Bruno .................. 604/274 |
| 4,411,656 | 10/1983 | Cornett, III ............ 604/212 |
| 4,417,887 | 11/1983 | Koshi .................. 604/162 |
| 4,425,120 | 11/1984 | Sampson et al. ........ 604/198 |
| 4,568,336 | 2/1986 | Cooper ................ 604/240 |
| 4,613,326 | 9/1986 | Szwarc ................. 604/89 |
| 4,623,336 | 11/1986 | Pedicano et al. ........ 604/192 |
| 4,643,199 | 2/1987 | Jennings, Jr. et al. .... 128/763 |
| 4,655,751 | 4/1987 | Harbaugh ............. 604/198 |
| 4,666,435 | 5/1987 | Braginetz ............. 604/198 |
| 4,681,567 | 7/1987 | Masters et al. ......... 604/198 |
| 4,702,738 | 10/1987 | Spencer ............... 604/198 |
| 4,702,739 | 10/1987 | Milorad ............... 604/198 |
| 4,723,943 | 2/1988 | Spencer ............... 604/198 |
| 4,737,144 | 4/1988 | Chokski .............. 604/198 |
| 4,738,663 | 4/1988 | Bogan ................ 604/198 |
| 4,747,830 | 5/1988 | Gloyer et al. .......... 604/110 |
| 4,747,837 | 5/1988 | Hauck ................ 604/198 |
| 4,790,827 | 12/1988 | Haber et al. ........... 604/198 |
| 4,801,295 | 1/1989 | Spencer ............... 604/198 |
| 4,865,592 | 9/1989 | Rycroft ............... 604/197 |
| 4,871,355 | 10/1989 | Kikkawa .............. 604/198 |
| 4,917,679 | 4/1990 | Kronner .............. 604/198 |
| 5,059,185 | 10/1991 | Ryan ................. 604/110 |
| 5,067,945 | 11/1991 | Ryan et al. ............ 604/198 |

FOREIGN PATENT DOCUMENTS

| | | | |
|---|---|---|---|
| 0331452 | 9/1989 | European Pat. Off. ............ 604/263 |
| 0339954 | 11/1989 | European Pat. Off. ............ 604/110 |

*Primary Examiner*—John D. Yasko
*Assistant Examiner*—V. Alexander
*Attorney, Agent, or Firm*—David P. Gordon

[57] ABSTRACT

A safety holder for a pre-filled medical syringe cartridge includes a barrel tube with a hinged locking gate and a safety sleeve. In one embodiment of the invention, the safety sleeve is a separate piece having interior surface projections and the barrel tube is provided with longitudinal and circumferential tracks on its outer surface. The separate safety sleeve slides over the barrel tube so that the interior surface projections engage the tracks. The tracks are provided with various locking configurations which engage the interior surface projections of the sleeve to hold it in a non-safety position while the syringe is being used and lock it in a safety position after use. A second embodiment of the invention includes an integral non-movable safety sleeve for use with IV administration line ports.

20 Claims, 7 Drawing Sheets

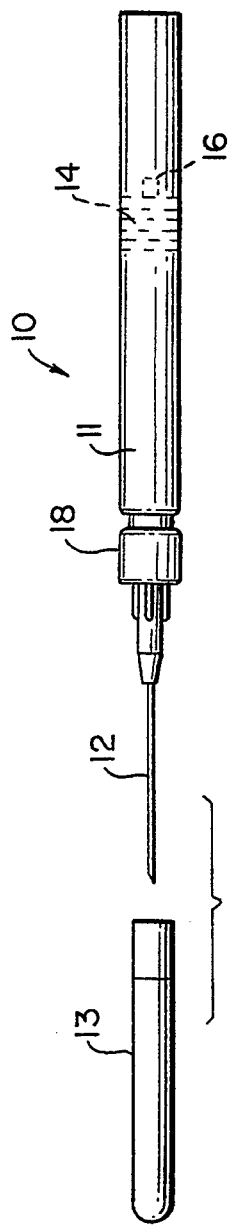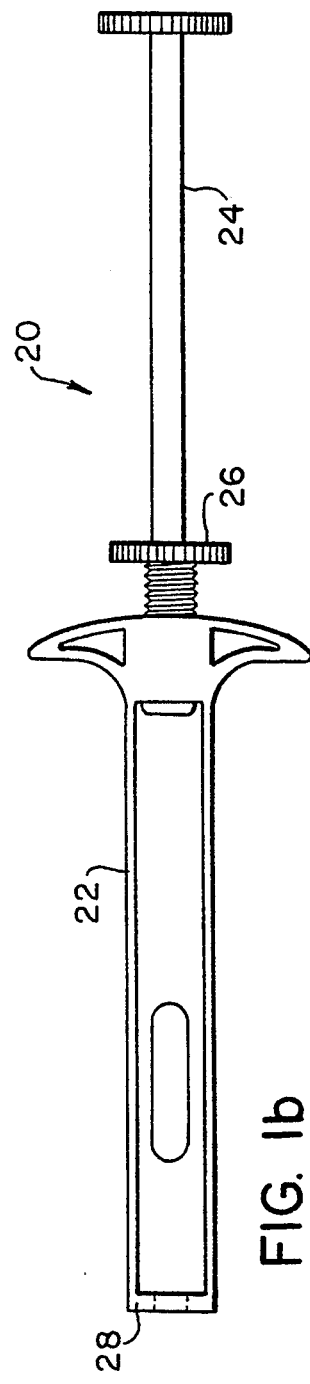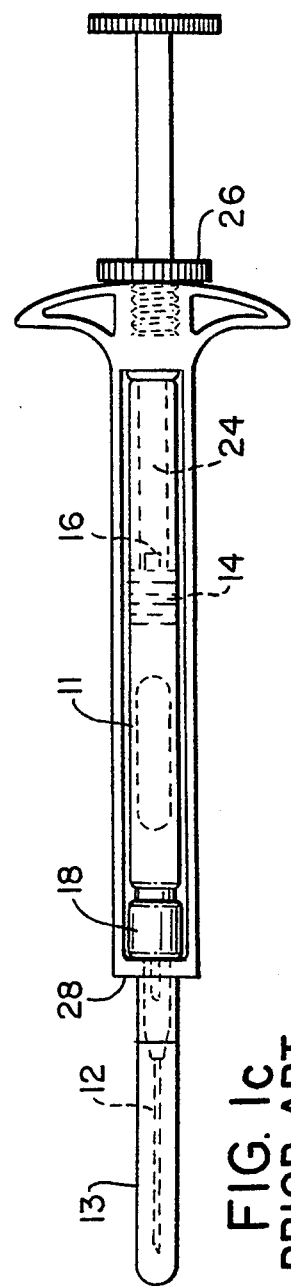
FIG. 1a PRIOR ART
FIG. 1b PRIOR ART
FIG. 1c PRIOR ART

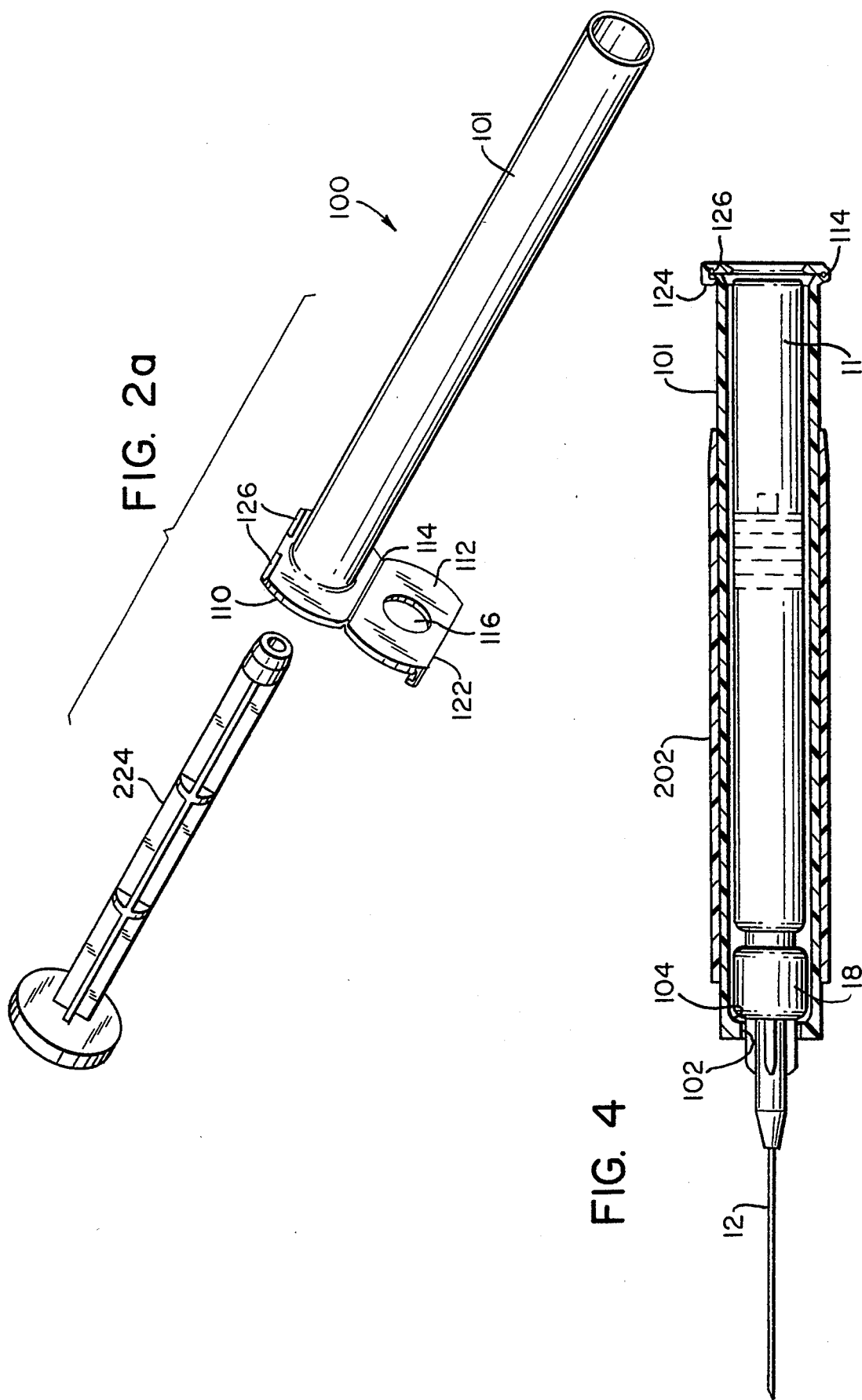

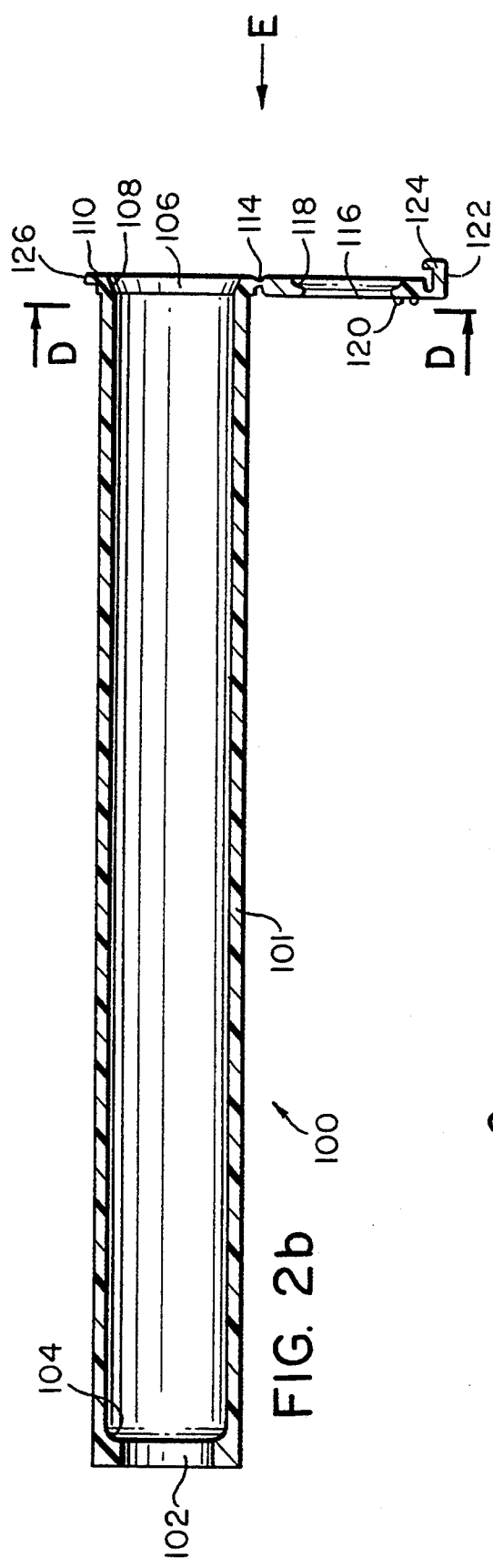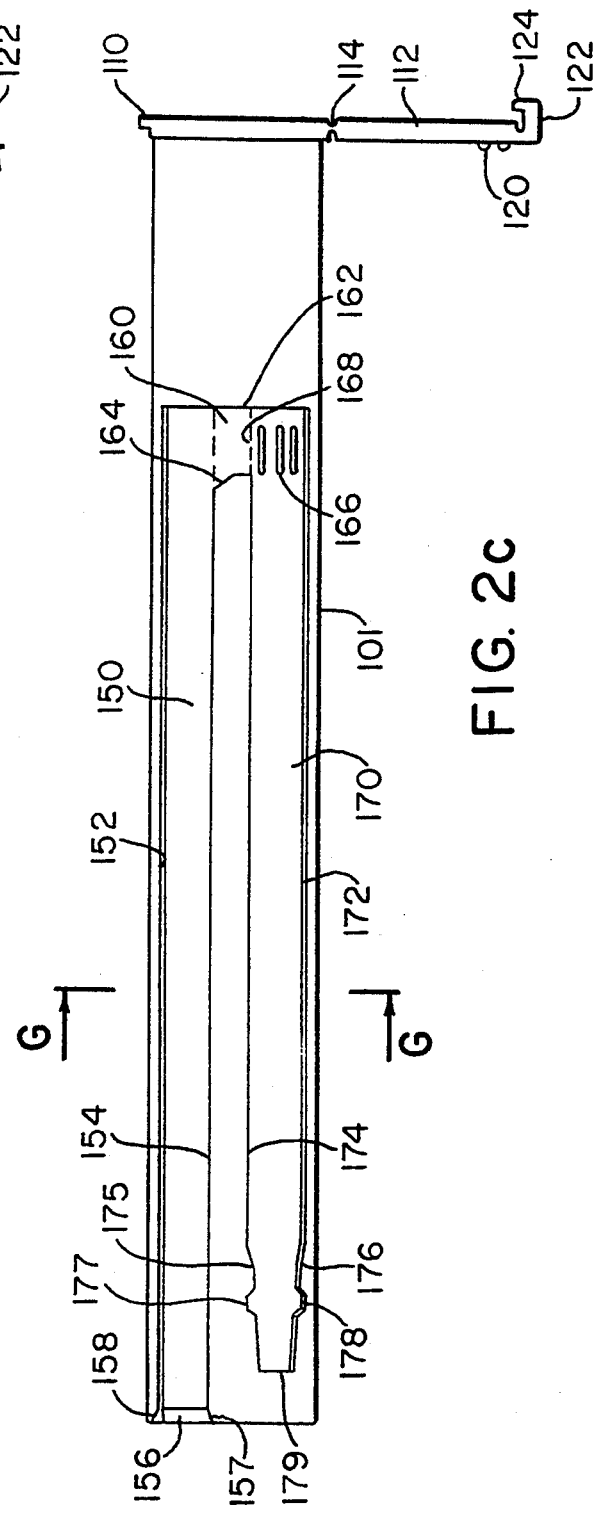

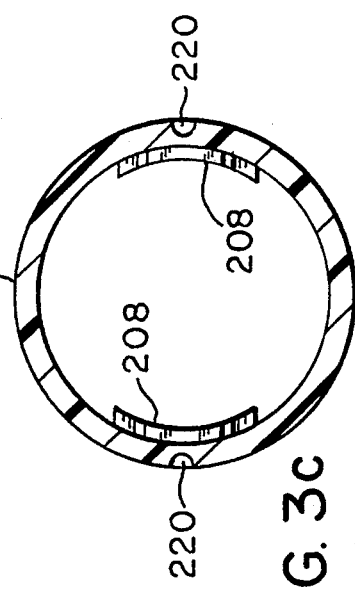
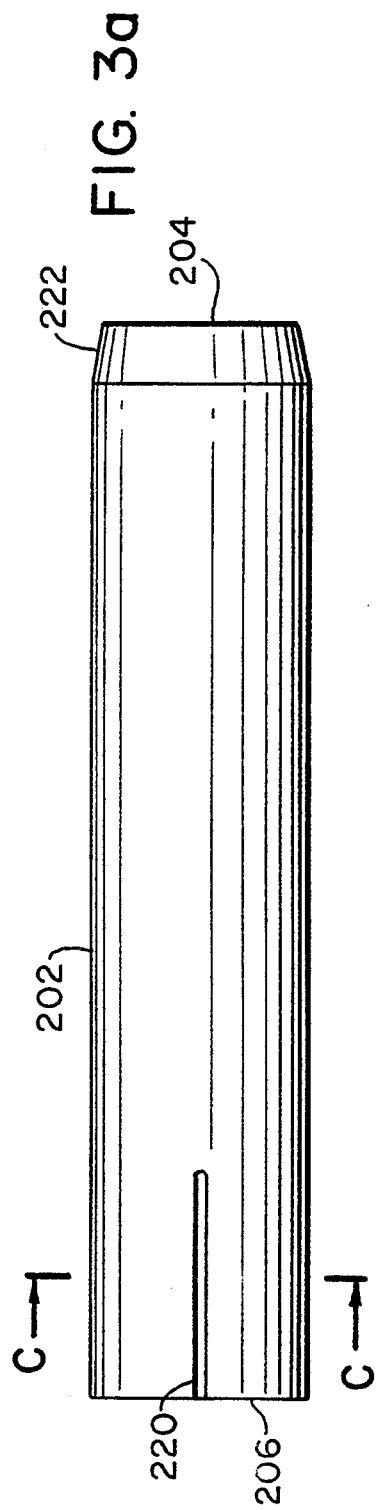
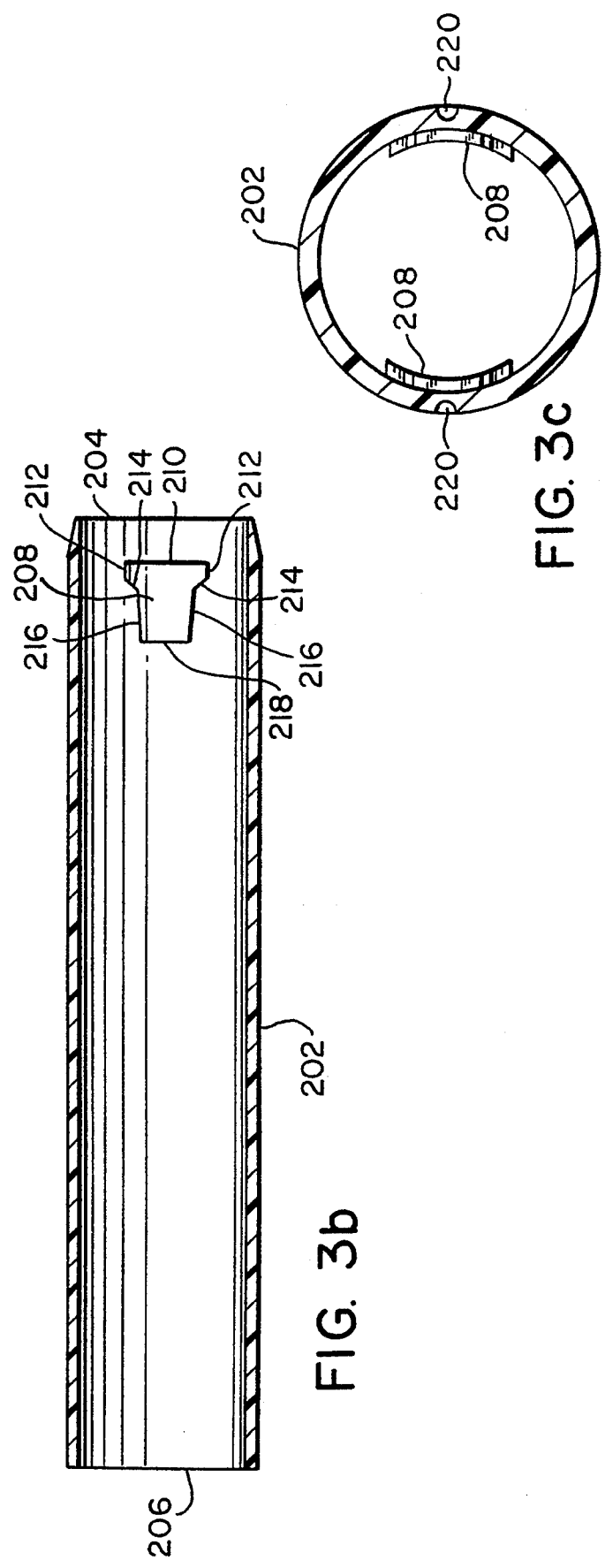

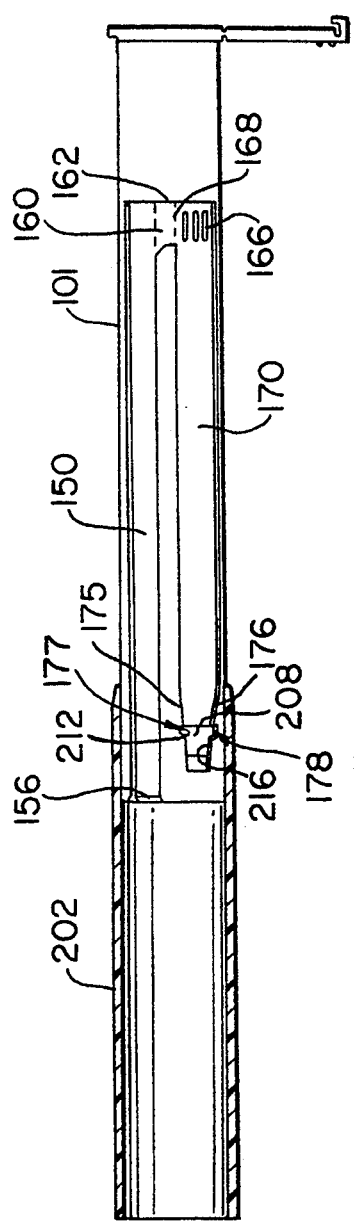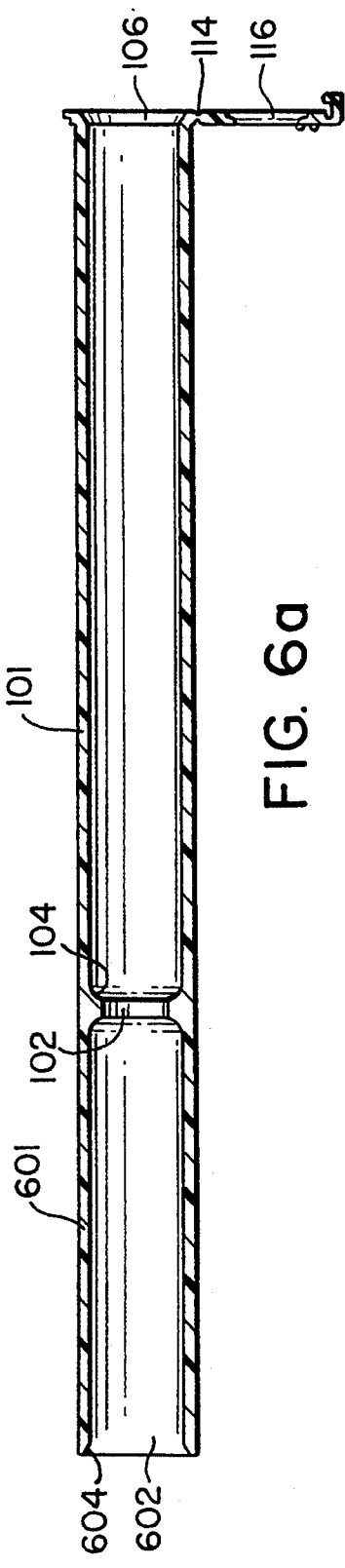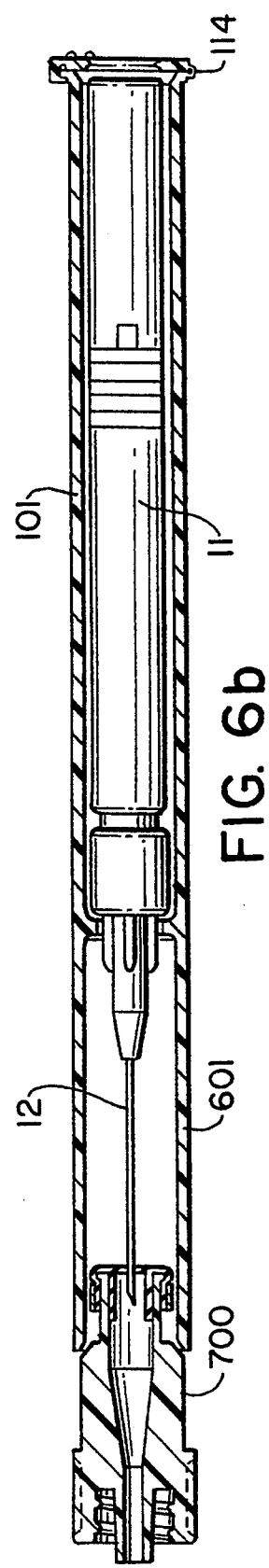

SAFETY HOLDER FOR PRE-FILLED DISPOSABLE SYRINGE CARTRIDGE

BACKGROUND OF THE INVENTION

1. Field of the Invention

The present invention relates to a holder for use with a disposable pre-filled syringe cartridge. More particularly, the present invention relates to a syringe barrel having a safety sleeve to prevent accidental needle sticks and abuse of the syringe.

2. State of the Art

Accidental needle sticks have long been a problem in the medical profession. They most often occur during the recapping of a contaminated needle or immediately after use and prior to safe disposal. Such needle sticks place the medical professional (clinician) at great risk. When needles are not recapped, additional needle sticks are caused by uncapped needles found in patient beds, linens, and in garbage cans, and place health care, housekeeping and sanitation personnel at risk. Because accidental needle sticks can now result in deadly incurable diseases as well as the previously appreciated serious, but curable diseases, the need for eliminating the needle stick problem has reached extreme urgency. In addressing the urgency, many devices have been proposed. Indeed, the prior art discloses a number of devices which are arranged to shield the needle of the syringe after use.

Safety-needled syringes are disclosed in U.S. Pat. Nos. 2,571,653 to Bastien, 4,026,287 to Haller, 4,425,120 to Sampson et al., 4,573,967 to Sampson et al., 4,631,057 to Mitchell et al., 4,643,199 to Jennings, Jr. et al., 4,655,751 to Harbaugh, 4,666,435 to Braginetz, 4,681,567 to Masters et al., 4,702,738 to Spencer, and 5,059,185 to Ryan. Most of these devices involve some kind of sleeve which slides into a locked position to cover the needle of the syringe. Some of the devices are quite complex and difficult to manufacture and some of the devices do not operate so well as to effectively lock the sleeve into position covering the needle.

In U.S. Pat. No. 4,425,120 to Sampson et al., for example, a complex arrangement of tracks including axial and circumferential components of shield and syringe members are required, making manufacture and assembly more difficult and expensive. Moreover, the sleeve which guards the needle is releasable from the safety position which is undesirable. It is preferred that the sleeve be locked in the safety position so that it is not inadvertently removed leaving the needle exposed. U.S. Pat. No. 4,631,057 to Mitchell et al. requires a collar member over which a shield slides. The device is complex, difficult to manufacture and assemble, and requires permanent attachment of the collar to the syringe tube. U.S. Pat. No. 4,573,967 to Sampson et al. requires additional intricate members which are attached to both the tube and the shield and which provide a locking action. The additional members are expensive to manufacture and assemble, unwieldy to handle, and would require a clinician to develop a new technique for utilization.

U.S. Pat. No. 4,655,751 to Harbaugh requires at least one slide groove to maintain the shield in the proper rotational axis and to thereby align a pair of ears on the shield with either one of two pairs of pockets in the outer surface of the syringe tube. Besides being relatively expensive to manufacture and assemble due to the ears and pockets, it also requires flexing of the shield to move it to the needle-shielding position, and thus has the potential for cracking or breaking. Moreover, the sleeve which guards the needle is releasable from the safety position which is undesirable. Similarly U.S. Pat. No. 4,681,567 to Masters et al. requires slide grooves in the shield and knobs or ears on the tube. Restrictions in the groove provide locking positions for the shield. Again, however, the knobs may be costly to manufacture and assemble and are prone to breaking. Also, it is not evident how such a device could be manufactured without sonically welding the shield around the tube, as any attempt to slide the shield over the tube and into a non-extended position would require overcoming the same locking action which is used to finally lock the shield relative to the tube.

U.S. Pat. No. 4,666,435 to Braginetz requires a complex and difficult to manufacture arrangement of tracks, rails, detents and stop surfaces which involves considerable expense to manufacture and assemble. Moreover, to lock the syringe tube and shield, the user must step through a predetermined sequence of relative rotational and longitudinal movements between the shield and the syringe tube. U.S. Pat. No. 2,571,653 to Bastien is simpler in design and has a single latch secured by a tensioning device to lock the shield at fixed points on the syringe tube, but the shield is not as secure in the safety position due to the single latch and any mishandling of the device could cause movement of the tensioning device and exposure of the needle.

U.S. Pat. No. 4,702,738 to Spencer shows a syringe with a pair of longitudinal grooves coupled by a circumferential groove and a shield having a protrusion or boss on its inner surface. The shield is mounted on the tube by engaging the boss in one of the longitudinal grooves and sliding the shield until the boss engages the circumferential groove. Rotating the shield allows the boss to engage the second longitudinal groove. The grooves are provided with cavities at different points wherein the boss my extend and somewhat lock the shield in a position and preferably in a locked position when the shield is extended over the needle. The grooves, boss, and cavities taught by Spencer, however, are schematic in nature and do not assure smooth and positive operation of the device.

U.S. Pat. Nos. 4,026,287 to Haller and 4,643,199 to Jennings, Jr. et al. show safety devices which utilize a technique of withdrawing the needle into the tube in order to render the needle harmless. These devices, and others like them typically require additional parts and are difficult to manufacture.

In recent years, pre-filled disposable syringe cartridges have been widely used. These syringes 10, as shown in prior art FIG. 1a, comprise a pre-filled ampoule 11 with an attached distal needle 12 (having a removable needle guard 13) and a proximal inserted rubber seal 14 having a threaded insert 16. Typically, the needle 12 is double pointed and mounted in a needle hub 18 covering a membrane seal on the ampoule. The pre-filled syringe 10 is inserted into a reusable holder 20, as shown in prior art FIGS. 1b and 1c, comprising a barrel 22 and a plunger rod 24. After insertion into the barrel 22, a locking screw 26 advances the syringe forward until shoulders 28 of the barrel engage the needle hub 18 and force the needle 12 towards the membrane seal thereby opening fluid communication between the needle 12 and the ampoule 11 and securing the syringe within the barrel 22. The plunger rod 24 is then threaded to the threaded insert 16 on the rubber plunger 14 of the ampoule 11 and movement of the plunger forward causes movement of the threaded insert 16 and the injection into the patient of the fluid in the ampoule.

As noted above, the needle guard 13 on pre-filled disposable syringe cartridges is simply a removable cap which frictionally engages the needle hub 18. Moreover, the known reusable holders for pre-filled syringe cartridges provide no safety means for covering the needle as it is expected that once the syringe is emptied, the needle will be recapped and the syringe removed from the reusable holder. Unfortunately, it is during this recapping and removal of the syringe that the danger of needle sticks is the greatest.

U.S. Pat. No. 5,059,185 addresses the use of safety shields for needled devices generally and includes a safety means for use with pre-filled disposable syringe cartridges. This earlier patent does not, however, deal in depth with the specific problems encountered with the use of pre-filled disposable syringe cartridges.

SUMMARY OF THE INVENTION

It is therefore an object of the invention to provide a disposable holder for pre-filled syringe cartridges which includes safety means to prevent accidental needle sticks.

It is also an object of the invention to provide a holder for pre-filled syringe cartridges which has few parts, is inexpensively manufactured and is easy to assemble.

It is another object of the invention to provide a holder for pre-filled syringe cartridges which includes a sliding safety sleeve which is locked in place when slid over the needle of an inserted syringe.

It is still another object of the invention to provide a single piece holder having an integral safety sleeve for pre-filled syringe cartridges used in conjunction with various IV administration line ports.

In accord with these objects which will be discussed in detail below, the disposable holder for pre-filled syringe cartridges of the present invention includes an injection molded syringe barrel in the form of a tube having an interior distal shoulder for engaging the needle hub of a pre-filled syringe cartridge and a proximal external finger flange. The external flange is coupled by a live hinge to a locking gate for securing the pre-filled syringe cartridge within the tube. The locking gate is provided with a central opening for receiving a plunger rod. As used herein, the term "proximal" means closest to the medical practitioner and farthest from the needle tip, while the term "distal" means farthest from the practitioner and closest to the needle tip.

In one embodiment, the tube is provided on its outer surface with two pairs of longitudinal tracks which are connected by a pair of ramped bridge tracks. A separate safety sleeve is provided having a pair of interior surface projections which engage and ride in the tracks. A first pair of longitudinal tracks ("assembly tracks") permit the safety sleeve to slide onto the tube for assembly; after which the safety sleeve is rotated so that its interior projections engage the ramped bridge tracks where it is held securely during injection. After injection, the safety sleeve is then slidable along the second pair of longitudinal tracks ("safety tracks") to a shielded position where it is locked into position by notched walls of the safety tracks which engage the interior projections of the sleeve.

In a second embodiment, the tube is provided with an integral safety collar which extends beyond the interior shoulder to surround the needle of an inserted syringe. The collar prevents accidental needle sticks, and has an inside diameter dimensioned to allow injection through various IV administration line ports which can be inserted into the collar.

Preferred aspects of the invention include: a plurality of ribs on the surface of the bridge tracks to secure the sleeve in the retracted or unshielded position while the syringe is used for injection; specially designed interior surface projections having wings and tapers which engage similarly shaped notches and tapers in the walls of the safety tracks to lock the sleeve in the shielded position; diametrical tapers at the distal ends of the assembly tracks to allow rapid attachment of the safety sleeve to the barrel tube; and exterior grooves opposite the interior surface projections of the sleeve to aid in automated assembly.

Additional objects and advantages of the invention will become apparent to those skilled in the art upon reference to the detailed description taken in conjunction with the provided figures.

BRIEF DESCRIPTION OF THE DRAWINGS

FIG. 1a is a side elevation view of a prior art pre-filled disposable syringe cartridge;

FIG. 1b is a side elevation view of the prior art reusable pre-filled syringe cartridge holder;

FIG. 1c is a view similar to FIGS. 1a and 1b showing the prior art pre-filled syringe cartridge mounted in the prior art holder;

FIG. 2a is a perspective view of a disposable pre-filled syringe cartridge holder according to the invention with a plunger rod;

FIG. 2b is a longitudinal cross sectional view of a first embodiment of a disposable pre-filled syringe cartridge holder according to the invention;

FIG. 2c is a side elevation view of the pre-filled syringe cartridge holder of FIG. 2b showing tracks on which a sliding sleeve is mounted;

FIG. 3a is a side elevation view of a safety sleeve used together with the pre-filled syringe cartridge holder of FIG. 2c;

FIG. 3b is a longitudinal cross section of the safety sleeve of FIG. 3a;

FIG. 3c is a cross sectional view of the safety sleeve of FIG. 3a along line C—C;

FIG. 4 is a side elevation view (transparent) of an assembled holder according to a first embodiment of the invention;

FIG. 5 is a view similar to FIG. 4 but without an inserted pre-filled syringe cartridge and with the safety sleeve in the safety position;

FIG. 6a is a longitudinal cross sectional view of a second embodiment of the disposable pre-filled syringe cartridge holder of the invention;

FIG. 6b is a side elevation view (transparent) of the embodiment of FIG. 6a, with the pre-filled syringe cartridge and IV administration line port in place.

DETAILED DESCRIPTION OF THE PREFERRED EMBODIMENT

Figure 2D:
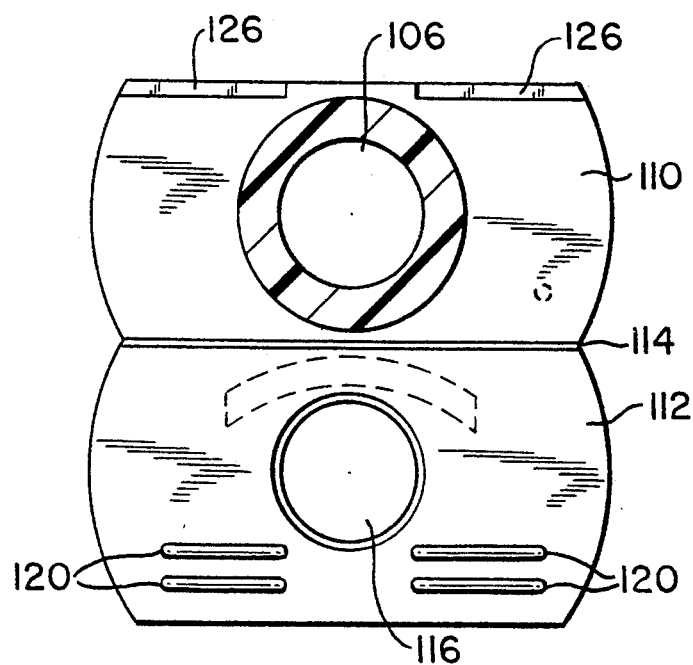
FIG. 2d is a cross sectional view of the tube of FIG. 2b along the line D—D showing the distal side of the flange.
Figure 2E:
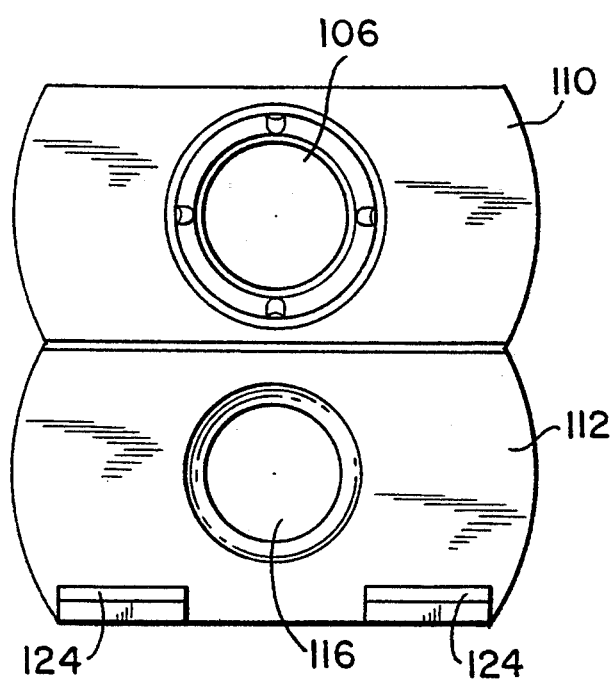
FIG. 2e is a side elevation looking in the direction E of FIG. 2b showing the proximal side of the flange.
Figure 2F:
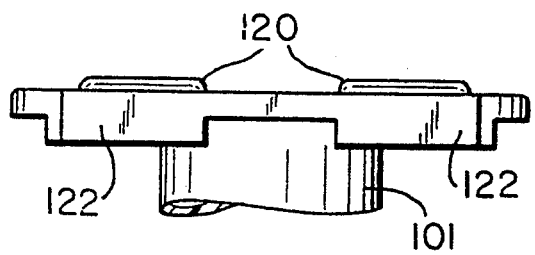
FIG. 2f is a side view of the flange with the locking gate closed.

Turning now to FIGS. 2a and 2b, a disposable pre-filled syringe cartridge holder 100 is preferably injection molded to form a hollow tube 101. The preferred material is a base resin co-polyproplyene polymer with a 0.25% to 0.50% synpro petrac slipeze slip agent. The length of the tube is typically approximately 3.349 inches and the inside diameter is typically approximately 0.379 inches, but as will be appreciated from the description which follows, the dimensions of the tube are dictated by the dimensions of the pre-filled syringe cartridge which will be used. The distal end of tube 101 has an opening 102 defined by an interior shoulder 104. The diameter of opening 102 (typically approximately 0.277 inches) is smaller than a conventional needle hub 18 (18 in FIGS. 1a and 1c). The proximal end of tube 101 is provided with an external integral finger flange 110 surrounding a proximal opening 106. Proximal opening 106 is defined by tapered wall 108 and has a diameter slightly larger than the external diameter of a conventional pre-filled syringe cartridge (11 in FIG. 1a). Flange 110 typically extends approximately 0.25 to 0.35 inches beyond the external surface of tube 101 in a substantially rectangular format as can be seen and is provided with a live hinge 114 beyond which lies a folding locking gate 112. Locking gate 112 is provided with an opening 116 defined by lip 118. Opening 116 has a smaller diameter (typically 0.271 inches) than the proximal opening 106, and is designed to be smaller than the outer diameter of a conventional pre-filled syringe cartridge ampoule. Locking gate 112 is also provided with one or more extensions 122 at its edge most distant from live hinge 114 (see also FIGS. 2e and 2f). Extensions 122 extend normally relative to gate 112 and terminate with an inward bent hook portion 124. The opposite edge of flange 110 is provided with one or more engaging edges 126 which when the hinged locking gate 122 is folded along live hinge 114 are grasped by hook portions 124 (see also FIGS. 2d and 2f). Due to the dimensions of the flange and locking gate and the configuration of the engaging edges and hook portions, it is difficult to unlock the locking hinge once it is folded into its locked position. In order to assist the manual movement of the locking gate 112 into the locked position, one or more ribs 120 are provided on its surface to be engaged by the thumb of a practitioner when snapping the locking gate into the locked position.

As will be appreciated from the above description (and as shown in FIG. 4), a conventional disposable pre-filled syringe cartridge can be inserted into tube 101 so that its needle 12 extends through opening 102 while its needle hub 18 is engaged by shoulder 104. Locking gate 112 can then be folded along live hinge 114 until hook portions 124 grasp engaging edges 126 thereby locking the pre-filled syringe cartridge inside the tube. By dimensioning the length of tube 101 appropriately, the action of folding locking gate 112 will cause the syringe needle hub to be biased against shoulder 104 and force the double pointed needle towards the membrane seal of the ampoule, thereby opening fluid communication between the needle and the ampoule. A plunger rod 224 (FIG. 2a) can then be inserted through openings 116 and 106 to threadably engage the syringe plunger in a conventional manner.

After assembly of the holder, pre-filled syringe cartridge, and plunger rod, injection is performed in a familiar manner. The practitioner grasps the tube 101 between index and middle finger, resting these fingers against finger flange 110. The practitioner then pushes plunger rod 24 with his/her thumb towards the flange 110. The plunger rod 24, being threaded to the plunger 14 of the pre-filled syringe cartridge 11, thereby pushes the fluid in the ampoule 11 out through the needle 12.

Figure 2G:
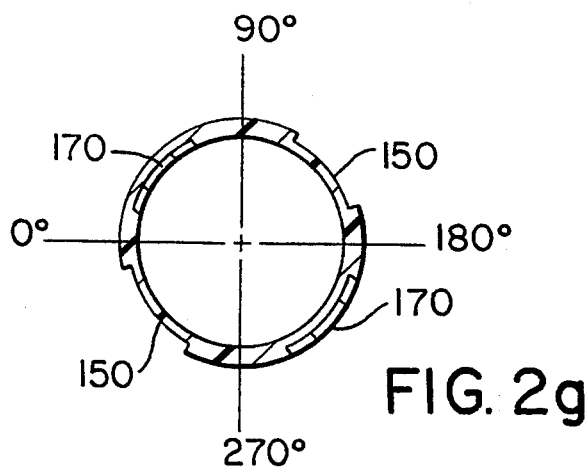
FIG. 2g is a cross sectional view of the tube of FIG. 2c along line G—G showing the radial locations of the assembly and safety tracks.

In accord with the preferred embodiments of the invention, different safety sleeves are provided for use with the tube described above. One preferred embodiment utilizes a sliding lockable safety sleeve. In particular, turning now to FIG. 2c, the same tube 101 as described above is shown in side elevation so that its exterior surface can be seen. The exterior surface of tube 101 is provided with four longitudinal tracks equally spaced around the circumference of the tube (see also FIG. 2g). These four tracks include two "assembly" tracks 150 (only one of which can be seen in FIG. 2c, the other one being spaced 180° apart on the opposite side of tube 101 as shown in FIG. 2g) and two "safety" tracks 170 (only one of which can be seen in FIG. 2c, the other one being spaced 180° apart on the opposite side of tube 101 as shown in FIG. 2g). Each "assembly" track 150 is joined to a corresponding "safety" track 170 as shown in FIG. 2c by a circumferential ramped bridge track 160.

Assembly tracks 150 are defined by two substantially parallel walls 152, 154 which extend from the distal end of tube 101 to points short of the proximal end of tube 101 as will be appreciated from the description which follows. At the distal end of tube 101, walls 152, 154 flare outward slightly at 157, 158 and taper inward radially to the tube at 156. Outer wall 152 extends somewhat longer than inner wall 154 and terminates at a substantially orthogonal circumferential wall 162 which defines ramped bridge track 160 as can be seen in FIG. 2c. Inner wall 154 extends somewhat shorter than outer wall 152 and terminates with an angled circumferential wall 164 which further defines ramped bridge track 160.

The dimensions of the assembly tracks are typically approximately 0.204 inches from outer wall 152 to inner wall 154 and approximately 2.280 inches from the distal end of tube 101 to circumferential wall 162. The depth of the tracks is typically approximately 0.014 inches. As will be appreciated from the description above, these tracks and the tracks described below are easily formed during the injection molding process of manufacturing tube 101.

Safety tracks 170 are defined by two substantially parallel walls 172, 174 which extend from the bridge track 160 to points short of the distal end of tube 101. The inner wall 174 extends from angled circumferential wall 164 and the outer wall 172 extends from substantially orthogonal circumferential wall 162 as seen in FIG. 2c. Walls 172, 174 terminate short of the distal end of tube 101 with tapers 175, 176 each incorporating ears or notches 177, 178 and joined by substantially orthogonal circumferential wall 179.

The dimensions of the safety tracks are typically approximately 0.204 inches from outer wall 172 to inner wall 174 and circumferential wall 179 is approximately 0.125 inches from the distal end of tube 101. The angles and lengths of the tapers 175, 176 and notches 177, 178 are better understood with reference to the safety sleeve described below in connection with FIG. 3.

Figure 2H:
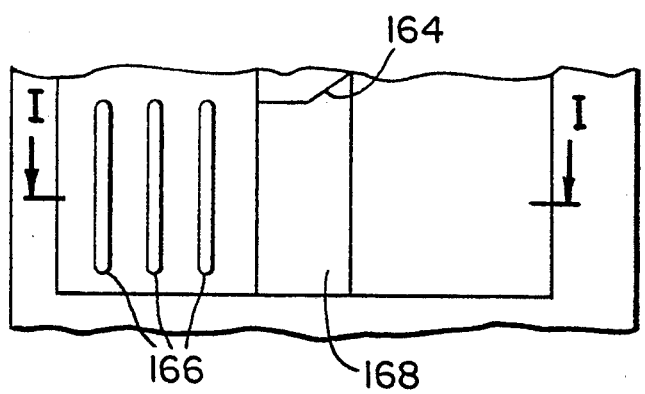
FIG. 2h is a close detail of the ramped bridge track of the tube of FIG. 2c.
Figure 2I:
FIG. 2i is a cross section along line I—I of FIG. 2h.

Ramped bridge tracks 160 are defined by substantially orthogonal circumferential wall 162 which joins outer wall 152 of assembly track 150 and outer wall 172 of safety track 170 and angled circumferential wall 164 which joins inner wall 154 of assembly track 150 and inner wall 174 of safety track 170. The bridge tracks are provided with a number of longitudinal ribs 166 lying substantially within the bounds of safety track 170 as seen in FIGS. 2c, 2h and 2i. Between ribs 166 and assembly track 150, bridge track 160 is provided with a ramped floor 168 which is seen best in FIG. 2i.

Turning now to FIGS. 2h and 2i, the depth of the bridge track is variable according to ramp 168. In the presently preferred embodiment, ramp 168 extends to a height of 0.010 inches from the surface of the assembly track in a circumferential distance of 0.1 inches. Previously mentioned longitudinal ribs 166 are typically 0.015 inches wide and extend from the floor of the bridge track to a height of 0.005 inches. They are evenly spaced at 0.05, 0.1, and 0.15 inches from the high end of ramp 168.

The angled wall portion 164 of the bridge track extends for 0.050 inches at an angle of 30° to the circumferential wall 162 and for 0.050 inches parallel to the circumferential wall 162.

Turning now to FIGS. 3a and 3b, a safety sleeve 202 for use with the tube embodiment of FIG. 2c is shown in side elevation and in longitudinal cross section. The safety sleeve is a hollow tube with a proximal opening 204, a distal opening 206, and an outer surface which is tapered at 222 of the proximal end. The most prominent feature of the sleeve is the interior surface projections 208 one of which can be seen in FIG. 3b, the other one being disposed 180° apart from it on the opposite inside surface of the sleeve as shown in FIG. 3c. The inside diameter of sleeve 202 (typically approximately 0.437 inches) is chosen so that the sleeve will fit comfortably over tube 101, the interior surface projections 208 extending into and riding along the tracks described above. Each projection 208 is therefore defined by a circumferential wall 210 which extends a width substantially equal to the width of notches 177, 178 described above and is typically 0.2 inches wide. Wall 210 is joined by two substantially parallel longitudinal walls 212 extending typically 0.04 inches followed by two angled walls 214 which typically have an angle of 45° to the longitudinal walls. The angled walls are followed by tapers 216 terminating in another circumferential wall 218 having a typical width of 0.14 inches, approximately 0.2 inches from the circumferential wall 210. The shape of this projection is chosen to correspond to the configuration of the distal end of safety track 170 described above and this can be appreciated by comparing FIGS. 3b and 2c. Also, in order to facilitate automated assembly of this embodiment of the invention, sleeve 202 may be provided with exterior grooves 220 indicating the internal positions of the projections 208 so that a machine can be used to mount the sleeves on the tubes.

A composite view of these features is shown in FIG. 5 where projection 208 is shown locked in position at the distal end of safety track 170. It will be appreciated that in assembly the sleeve 202 is mounted on tube 101 by inserting projections 208 over tapered portions 156 of assembly tracks 150 and by sliding the sleeve until the projections abut circumferential wall 162. The sleeve is then rotated so that projections 208 ride over the ramp 168 described above. Longitudinal ribs 166 then engage projections 208 to hold the sleeve in the non-safety position while the needle is being used as shown in FIG. 4. It is anticipated that the attachment of the safety sleeve to the tube will be accomplished during manufacturing and the practitioner will not need to perform this step. The practitioner will, however, insert a pre-filled disposable syringe cartridge into the proximal opening 106 of the tube 101, fold the locking gate 112 to lock the syringe cartridge in the tube and attach a plunger rod 224. Injection can then be performed in the familiar manner described above. After injection, the safety sleeve is slid with the projections 208 riding in safety track 170 until tapers 216 of projections 208 enter between tapers 175, 176 of track 170. Longitudinal walls 212 of projections 208 are progressively biased as they engage tapers 175, 176 when the sleeve is slid further towards the distal end of tube 101. Ultimately, the projections 208 are locked in place as shown in FIG. 5 when the longitudinal walls 212 of projections 208 pass along tapers 175, 176 of track 170 to engage notches 177, 178.

A second embodiment of the invention which is preferably used with pre-filled syringe cartridges having a five-eighths inch needle or smaller having medication for dispensing through an IV line administration port such as a PRN device is shown in FIGS. 6a and 6b. FIG. 6a shows a tube 101 substantially the same as the tube 101 of FIG. 2. This embodiment of tube 101, however, does not have the tracks described in FIG. 2c; rather it is provided with an integral molded extension 601 extending beyond the previously distal opening 102 of tube 101 to a new distal opening 602 defined by a flared inner wall 604. FIG. 6b shows the position of a pre-filled disposable syringe cartridge 11 within this embodiment of the invention. In this embodiment, needle 12 is always covered by the extension 601 so that it is always protected from accidental needle sticks. However, the inner diameter of the new distal opening 602 is typically approximately .379 inches which is ideal for use with a PRN device 700 or other IV line administration port. As will be appreciated by those skilled in the art, even though the needle 12 is covered by extension 601, a PRN device 700 will fit inside opening 602 so that it may be injected with needle 12.

There have been described and illustrated herein different embodiments of a safety holder for a pre-filled medical syringe cartridge. While particular embodiments of the invention have been described, it is not intended that the invention be limited thereto, as it is intended that the invention be as broad in scope as the art will allow and that the specification be read likewise. Thus, while particular dimensions have been disclosed, it will be appreciated that other dimensions could be utilized to achieve substantially the same results once the invention is understood. Also, while particular hinge arrangements have been shown, it will be recognized that other types of hinges could be used with similar results obtained. Moreover, while particular configurations have been disclosed in reference to the assembly, bridge, and safety tracks, it will be appreciated that other configurations could be used as well. Furthermore, while the invention has been disclosed as being injection molded of certain materials, it will be understood that different materials and methods of manufacture can achieve the same or similar functions as disclosed herein. Also, while particular configurations of the finger flange have been shown as substantially rectangular, it will be appreciated that the finger flange could be other shapes and that the finger flange could be incorporated as part of the locking gate using different hinge means. While a finger flange has been described as providing a hinge and locking means for engaging the attached locking gate, it will be appreciated that the hinged locking gate could itself act as any needed "finger" flange and the locking gate could be hinged to the proximal end of the tube in another manner with other locking means provided at the proximal end of the tube. It will therefore be appreciated by those skilled in the art that yet other modifications could be made to the provided invention without deviating from its spirit and scope as so claimed.

I claim:

1. A disposable safety holder for a disposable pre-filled medical syringe cartridge having a pre-filled ampoule with a needle hub and an attached needle, said holder comprising:
   a) a hollow tube having a proximal end with a proximal opening which receives said syringe, and a distal opening;
   b) an interior shoulder adjacent said distal opening, wherein said interior shoulder engages said needle hub;
   c) hinge means coupled to a proximal end of said tube;
   d) gate means coupled to said hinge means and provided with locking means, wherein said gate means is movable from a first position where said proximal opening is unobstructed to a second locking position covering said proximal opening, and said gate means has an opening smaller than said proximal opening, whereby said gate means engages said ampoule when said gate means is moved to said second position;
   e) safety sleeve means extending from said hollow tube for covering said needle.

2. A disposable safety holder according to claim 1, wherein:
   said safety sleeve means is an integral component extending from said distal opening of said tube.

3. A disposable safety holder according to claim 1, wherein:
   said safety sleeve means is coaxially slidable relative to said tube.

4. A disposable safety holder according to claim 2, wherein:
   said safety sleeve means has a distal opening with an interior diameter dimensioned to receive an IV administration line port.

5. A disposable safety holder according to claim 3, further comprising:
   f) track means disposed on an exterior surface of said tube;
   g) surface projection means disposed on an interior surface of said safety sleeve, wherein said surface projection means slidably engages said track means.

6. A disposable safety holder according to claim 5, wherein:
   said track means comprises a first longitudinal track, a second longitudinal track, and a circumferential track,
   said first longitudinal track extending from said distal opening a first longitudinal distance to a first point between said distal opening and said proximal opening,
   said circumferential track extending from said first longitudinal track a first circumferential distance;
   said second longitudinal track extending substantially parallel to said first longitudinal track from said circumferential track a second longitudinal distance to a second point between said distal opening and said first point,
   said second longitudinal track comprising a pair of parallel walls extending from said circumferential track a third longitudinal distance to a third point between said first point and said second point and a pair of angled walls which angle towards each other as they extend from said third point to said second point, said angled walls having at least one notched opening.

7. A disposable safety holder according to claim 6, wherein:
   said circumferential track is provided with a ramped floor between said first longitudinal track and said second longitudinal track, said ramped floor rising in a direction from said first longitudinal track toward said second longitudinal track.

8. A disposable safety holder according to claim 7, wherein:
   said circumferential track has an angled wall portion adjacent said first longitudinal track such that said circumferential track is wider adjacent said first longitudinal track than adjacent said second longitudinal track.

9. A disposable safety holder according to claim 7, wherein:
   said second longitudinal track is provided with a plurality of longitudinal ribs in a portion of said second longitudinal track which intersect said circumferential track.

10. A disposable safety holder according to claim 1, further comprising:
    f) a finger flange surrounding said proximal opening, wherein said hinge means is coupled to said finger flange, and said gate means engages said finger flange in said second locking position.

11. A disposable safety holder according to claim 10, wherein:
    said hinge means is coupled to said finger flange at a first edge of said finger flange and said gate means engages said finger flange at a second edge of said finger flange, said second edge of said finger flange being parallel to said first edge of said finger flange.

12. A disposable safety holder according to claim 11, wherein:
    said hinge means is coupled to said gate means at a first edge of said gate means and said gate means is provided with a hook-like projection extending from a second edge of said gate means, said second edge of said gate means being parallel to said first edge of said gate means.

13. A disposable safety holder according to claim 1, wherein:
    said gate means comprises finger flange means when said gate means is in said second position.

14. A disposable safety holder for a disposable pre-filled medical syringe cartridge having a pre-filled ampoule with a needle hub and an attached needle, said holder comprising:

a) a hollow tube having a proximal opening for receiving said syringe, and a distal opening for exposing said needle;
b) a sliding sleeve coaxial to said tube and slidable relative to said tube from a non-safety position wherein said needle is exposed to a safety position wherein said needle is covered by said sleeve, said sliding sleeve having an interior surface projection;
c) a first longitudinal track disposed on an exterior surface of said tube, with said first longitudinal track extending from said distal opening a first longitudinal distance to a first point between said distal opening and said proximal opening;
d) a circumferential track disposed on said exterior surface of said tube, with said circumferential track extending from said first longitudinal track a first circumferential distance; and
e) a second longitudinal track disposed on said exterior surface of said tube, with said second longitudinal track extending substantially parallel to said first longitudinal track from said circumferential track a second longitudinal distance to a second point between said distal opening and said first point, and said second longitudinal track comprising a pair of parallel walls extending from said circumferential track a third longitudinal distance to a third point between said first point and said second point and a pair of angled walls which angle towards each other as they extend from said third point to said second point, said angled walls having at least one notched opening, wherein
said interior surface projection engages said first longitudinal track when said sliding sleeve is assembled on said hollow tube, said interior surface projection engages said circumferential track prior to said sliding sleeve being slid forward on said hollow tube, said interior surface projection engages said second longitudinal track when said sliding sleeve is slid forward on said hollow tube to shield the needle of the pre-filled medical syringe, and said interior surface projection locks in said notch in said pair of angled walls to lock said sliding sleeve in a shielding position on said hollow tube with said hollow tube shielding said needle of the pre-filled medical syringe.

15. A disposable safety holder according to claim 14, wherein:
said circumferential track is provided with a ramped floor between said first longitudinal track and said second longitudinal track, said ramped floor rising in a direction from said first longitudinal track toward said second longitudinal track.

16. A disposable safety holder according to claim 15, wherein:
said circumferential track has an angled wall portion adjacent said first longitudinal track such that said circumferential track is wider adjacent said first longitudinal track than adjacent said second longitudinal track.

17. A disposable safety holder according to claim 15, wherein:
said second longitudinal track is provided with a plurality of longitudinal ribs in a portion of said second longitudinal track which intersect said circumferential track.

18. A method of using a disposable pre-filled medical syringe cartridge having a pre-filled ampoule with a plunger, a needle hub and an attached needle, said method comprising the steps of:
a) providing a hollow tube having a proximal opening for receiving said syringe and a distal opening and an interior shoulder adjacent said distal opening for engaging said needle hub;
b) inserting said syringe into said proximal opening so that said needle hub is engaged by said interior shoulder;
c) providing a lockable gate means having a central opening for receiving a plunger rod;
d) locking said gate means over said proximal opening so that said gate means engages said ampoule and biases said ampoule towards said needle hub to open fluid communication between said ampoule and said needle;
e) inserting said plunger rod through central opening of said gate means;
f) attaching said plunger rod to said plunger;
g) pushing said plunger into said central opening to force fluid in said ampoule through said needle.

19. A method according to claim 18, further comprising:
h) providing said hollow tube with a sliding safety sleeve slidable from a first position in which said needle is exposed for injection to a second position in which said needle is covered by said sleeve; and
i) after forcing said fluid through said needle, sliding said sleeve from said first position to said second position.

20. Method according to claim 18, further comprising:
h) providing an integral extension extending from said distal opening of said tube so that said needle is shielded by said extension; and
i) prior to forcing said fluid through said needle, inserting an IV administration line port into said extension so that it is pierced by said needle.

* * * * *